United States Patent [19] [11] 4,278,667
Madison et al. [45] Jul. 14, 1981

[54] METHOD OF TREATING TARDIVE DYSKINESIA BY ORAL DOSAGE FORM OF A PHYSOSTIGMINE COMPOUND

[75] Inventors: James B. Madison, Maryland Heights, Mo.; Larry K. Hiland, Edwardsville, Ill.

[73] Assignee: Chromalloy American Corporation, St. Louis, Mo.

[21] Appl. No.: 155,479

[22] Filed: Jun. 2, 1980

[51] Int. Cl.³ .................... A61K 31/40; A61K 31/625
[52] U.S. Cl. .................................... 424/232; 424/274
[58] Field of Search ................................ 424/232, 274

[56] References Cited
PUBLICATIONS
Chem. Abst., vol. 77, (1972), 109436(h).

Primary Examiner—Stanley J. Friedman
Attorney, Agent, or Firm—Haverstock, Garrett & Roberts

[57] ABSTRACT

This invention relates to the use of a physostigmine compound in oral dosage form for the relief, cure or remission of tardive dyskinesia in living animal bodies. The physostigmine compounds include physostigmine, the salts of physostigmine and the esters of physostigmine. The oral dosage form may be in the form of tablets, coated or uncoated, capsules, liquids, powders and any other form of oral dosage which can be ingested into the living animal body. Physostigmine is also known as eserine.

10 Claims, No Drawings

METHOD OF TREATING TARDIVE DYSKINESIA BY ORAL DOSAGE FORM OF A PHYSOSTIGMINE COMPOUND

PRIOR ART AND BACKGROUND OF THIS INVENTION

Tardive dyskinesia consists of abnormal, involuntary movements usually of oral facial musculature but often involving the trunk and extremities. There is no known cure for this involuntary movement disorder, and it is usually irreversible. Therefore, prevention is the presently known effective method for dealing with the problem. Tardive dyskinesia often occurs in geriatric patients who have been taking neuroleptic drugs. In recent years, the greater use of psychotropic drugs has aggravated the incidence of tardive dyskinesia.

The typical oral facial movements include puffing of the checks, grimacing, protrusion and licking of the tongue, and chewing movements of the jaw and frequent incessant blinking of the eyes. The abnormal movements are rhythmic and repetitive and may interfere with speech, salivation, chewing, and swallowing. The patient may not even be aware of their presence. Tardive dyskinesia usually appears after months or years of treatment with neuroleptic drugs but it may develop after only a few weeks of such treatment. All neuroleptic drugs may cause tardive dyskinesia. However, the low-dose high potency drugs which produce the greatest degree of blockage, and thus a greater degree of extra pyramidal side effects are the most likely to cause tardive dyskinesia. Such high potency drugs include the phenothiazines, the thioxanthenes, the butyrophenones, the behzodiazepines and the dihydroindolones. The increasing use of neuroleptic drugs in geriatric care facilities has resulted in dramatic increase in the incidence of tardive dyskinesia. See Geriatrics, Volume 34, Number 7, pages 59–66, July 1979, by Harcourt Brace Jovanovich, Inc.

It has recently been discovered that cholinergic as well as dopaminergic systems may be involved in extrapyramidal movement disorders such as tardive dyskinesia. This lead to the investigation of anticholinergic drugs. It is reported in American Journal of Psychiatry, Volume 134, Number 7, July 1977, pages 769–774 that the use of physostigmine injections and choline have a positive therapeutic effect on tardive dyskinesia. Although the data presented is not clear, tests have shown that physostigmine injections reduce tardive dyskinesia movements in from 20% to 80% of patients suffering from tardive dyskinesia.

Further tests have been made with lecithin. Preliminary tests have indicated that patients with tardive dyskinesia who were treated by ingesting lecithin (phosphatidyl choline) over a 14 day period experienced significant improvement. See Science News, Volume 116, page 393, Dec. 8, 1979.

Recently, it has been demonstrated that injections of physostigmine salicylate have relieved the symptoms of tardive dyskinesia. However, the use of injectable forms of physostigmine compositions is not practical for useful therapy because the action of the physostigmine salt has a duration of not longer than 2 hours. The physostigmine salt is thus metabolized in the human body rapidly, in about 60–120 minutes. For treatment of tardive dyskinesia this would require injection every 2 hours, which treatment is not considered practical by physicians.

Physostigmine was first isolated in 1864 by Jobst and Hesse after it was originally introduced into England in the form of the calabar bean, in 1840, by Daniell, a British medical officer. During the last century, physostigmine has been used as a treatment for glaucoma and in post-operative ileus, and in the reversal of atropine-induced coma. More recently, physostigmine has been used effectively as an antidote to several drugs possessing central anticholinergic properties. See Journal Of The American College Of Emergency Physicians and University Association For Emergency Medical Services, June, 1976, Volume 5, Number 6, pages 436–439. Pediatrics, Volume 52, Number 3, September, 1973 discusses the use of physostigmine compounds such as physostigmine salicylate in the treatment of anticholinergic poisoning. The use of physostigmine in the treatment of anticholinergic poisoning is also discussed in Journal of The American College Of Emergency Physicians And University Association For Emergency Medical Services, Volume 5, Number 2, February, 1976, pages 125–127 wherein it is noted that drugs with anticholinergic effects are readily available to the public by prescription and over-the-counter and are increasingly the subject of abuse by the patients. This article discusses the use of physostigmine as an emergency antidote. The Journal Of The American College Of Emergency Physicians And University Associations For Emergency Medical Services, Volume 5, Number 6, June, 1976, pages 443–445 also discusses the use of physostigmine in the treatment of tricyclic antidepressant overdoses. The use of physostigmine compounds to reverse the effect of scopolamine in parturients is described in the American Journal of Obstetrics And Gynecology, Volume 116, Number 3, pages 326–329, June 1, 1976 and in The Journal Of International Anesthesia Research Society, Volume 55, Number 4, July–August, 1976. Thus, the use of physostigmine compounds to counteract the undesirable anticholinergic effect of many useful drugs has been known for a number of years and is growing in utilization by physicians.

BRIEF DESCRIPTION OF THE INVENTION

This invention relates to a method of treating tardive dyskinesia in living animal bodies comprising ingesting into such living animal bodies in the oral dosage form an effective amount of physostigmine compound for the relief, cure, or remission of the tardive dyskinesia. The physostigmine compound may be physostigmine, esters of physostigmine or salts of physostigmine.

Thus, it is a principal object of this invention to provide a method for treating tardive dyskinesia in a living animal body by means of the ingestion in an oral dosage form of a physostigmine compound.

It is a more specific object of this invention to treat tardive dyskinesia in a living animal body by means of the ingestion of a physostigmine compound in the form of a powder, a tablet, a liquid, or a capsule.

Another object of this invention is to provide a means for the self treatment of living animal bodies suffering from tardive dyskinesia by ingesting in oral dosage form an effective amount of a physostigmine compound.

DETAILED DESCRIPTION

This invention includes the use of oral physostigmine compounds, including physostigmine, the salts of physostigmine, and the esters of physostigmine, in the form of tablets, powders, liquids, or capsules, for use in the treatment of tardive dyskinesia.

The salts or esters of physostigmine useful in the practice of this invention are physostigmine salicylate, physostigmine sulfite, and physostigmine sulfate.

Physostigmine is an alkaloid obtained from the calabar bean having the following formula:

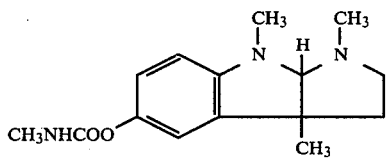

The physostigmine compounds of this invention are generally used in pure form. The preferred physostigmine compound is physostigmine salicylate. A particularly useful, presently commercial physostigmine salicylate is Antilirium, marketed by O'Neal, Jones and Feldman Division of Chromalloy American Corporation. Relatively pure physostigmine is generally available. Physostigmine sulfite is commercially available and useful in the practice of this invention. Physostigmine maleate is also available and useful in the practice of this invention. Other available esters and salts of physostigmine may be used in the practice of this invention. Also, various combinations of physostigmine compounds are useful. For example, physostigmine and physostigmine salicylate can be used in combination and some residual physostigmine may be present in commercially available physostigmine salicylate. Since the several physostigmine compounds noted herein are generally about equally effective in alleviating the condition of tardive dyskinesia, various combinations can be employed and the proportions are relatively unimportant.

The oral dosage forms containing a physostigmine compound may contain various inert additives and diluents. When the physostigmine compound is in the form of a compressed tablet, or in the form of pellets contained in a capsule, the tablets and pellets may be coated or uncoated and may contain enteric coatings for time release within the living animal bodies. Enteric coatings are well known in the art and are generally gelatinous materials which dissolve under specific conditions found within the alimentary tract of living animal bodies. Such dissolution may be based on temperature within the living animal body and release may be based on particular conditions of the chemistry existing in the various segments of the alimentary canal. For example, the pH of the stomach will be slightly acid and the alkalinity will generally increase as ingested materials traverse the alimentary tract through the stomach, the small intestine and the colon.

The oral dosage form of physostigmine compounds of this invention may also be in the form of a liquid, which may be a water solution or a syrup with a viscous syrupy base.

Further, the physostigmine compounds of this invention may be in the form of a powder which can be given to the patient in a solution or with other ingredients. When the powder form of composition is used, it may be necessary to package the powder in specific packets in order to avoid any possibility of overdose of the physostigmine compound which can lead to serious side effects and even death. The dosage which is generally acceptable will depend some what on the body weight of the living animal body ingesting the physostigmine compounds.

This invention includes the use of physostigmine compounds in various oral compositions in the treatment of tardive dyskinesia. The oral physostigmine compositions of this invention may contain from 0.5 to 32.0 milligrams of active physostigmine compounds. Dosages containing the larger amounts of physostigmine compounds will generally be used to treat larger living animal bodies since there is a relationship between the size of the living animal body and the amount of physostigmine compound which is necessary to be effective and which can be ingested without harmful effects. Smaller living animal bodies will require less active physostigmine compound for effective dosage. The relationship of dosage to the mass of living animal body can be controlled by providing a dosage form containing relatively low amounts of physostigmine compounds and by prescribing the proper number of dosages in a proper timing sequence to effect maximum effectiveness for each particular living animal body. A particular useful dosage may contain from 1.0 to 16.0 milligrams of active physostigmine compounds. Most living animal bodies may be treated effectively and safely with dosages containing from 1.0 to 8.0 milligrams of active physostigmine compounds. The safest dosage for general use will contain from 1.0 to 2.0 milligrams of active physostigmine compounds. In general, the physostigmine compounds will be ingested into the living animal body in an amount ranging from about 0.000002 percent to about 0.000064 percent by weight of living animal body.

EXAMPLES

Tests have been conducted to show the efficacy of this invention.

An open trial using Antilirium tablets, which contain one milligram each of active physostigmine salicylate in 158 milligrams of inert carrier, was completed using six subjects with tardive dyskinesia. Generally, the subjects tolerated dosages of 15 to 18 milligrams daily of physostigmine salicylate given in three divided doses at 9 a.m., 1 p.m., and 5 p.m. with minimal side-effects. Essentially the only side-effect which was noticed at three dosages was salivation. Other side-effects, including perspiration and urinary frequency, were seen at doses above 18 milligrams daily, and the one patient who received 27 and 30 milligrams daily experienced some nausea and vomiting.

The improvement in movement disorder was optimal at 15 and 18 milligrams of physostigmine salicylate daily and appeared to deteriorate with higher dosages. This deterioration may be related to increasing side-effects with higher dosages.

One patient entered the study immediately after cessation of neuroleptic medication. This was the only subject who showed no response to orally ingested physostigmine compounds.

Experience so far and clinical impressions are that any effects which have been noted are entirely reversible upon discontinuation of the drug and that this reversal occurs within a day of discontinuation. In addition, the effects of the drug appear to be sustained through the four hour interval between doses (9 a.m., 1 p.m., 5 p.m.). As tardive dyskinesia patients usually have no involuntary movements during sleep, this dosage schedule seems to be most useful.

The purpose of this study is to determine if physostigmine compounds, which reduce the involuntary movements of tardive dyskinesia when given intravenously, will have the same effect when given orally.

Tardive dyskinesia is believed to be caused by post-synaptic dopamine receptor hypersensitivity in the nigrostriatum. This hypersensitivity is induced by chronic treatment with neuroleptic drugs. As with other nigrostriatal movement disorders, the balance between acetyl cholinergic and dopaminergic neural systems appears to be disturbed in tardive dyskinesia. Tardive dyskinesia is believed to be the result of an overactive dopaminergic system, with a relatively underactive cholinergic system.

Efforts to treat these apparently reciprocal disorders have focused on shifting the DA-ACh balance more toward the normal state through alterations in either the dopamine or acetyl choline systems, independently or together. Physostigmine is an acetyl cholinesterase inhibitor. By inhibiting this enzyme, which destroys acetyl choline and thereby reduces the amount of this transmitter available at post-synaptic neurons with cholinergic input, the pharmacologic action of this drug is to increase the amount of acetyl choline available in the nigrostriatum and elsewhere, thus facilitating cholinergic transmission.

A clinical trial was completed of the use of oral physostigmine compounds in six patients. All of the patients were adult males weighing from 150 to 200 pounds. This was an open, uncontrolled trial in which patients received doses of physostigmine salicylate in the form of Antilirium tablets commencing at 6 milligrams daily and escalating gradually by 3 milligrams daily increments to a maximum of 30 milligrams daily. Significant side-effects were observed with the higher doses, as was a deterioration in the movement disorder, so that only two of the patients were given doses higher than 18 milligrams daily. None of the patients had significant side-effects other than salivation at doses of 15 milligrams or less daily. Five of the patients showed improvement in their movement disorder and one showed no change during the physostigmine trial. None showed worsening of the movement disorder on daily doses less than 18 milligrams.

In the present clinical trial the frequency of involuntary tongue movements is used as a standard for comparison. In the oral dosage physostigmine study 4 of 4 patients showed a reduction of tongue movements. Generally, the reduction in movement frequency was clinically very significant in the physostigmine compound treated subjects.

In addition, this clinical trial showed a decrement in response with higher doses similar to that seen in previously published studies of intravenous physostigmine compounds, and this decrement corresponded with the increase in side-effects seen with larger doses.

The results are summarized in table 1 wherein the physostigmine compound was Antilirium tablets containing 1 milligram of physostigmine salicylate in 158 milligrams of inert carriers given in equal amounts of five tablets each at 9 a.m., 1 p.m., and 5 p.m. to provide a total dosage of 15 milligrams daily for each subject. The subjects were all adult males weighing from 150 to 200 pounds.

TABLE 1

| Patient | Pretreatment TPF* | Posttreatment TPF* | % of pretreatment frequency |
|---|---|---|---|
| 1. | 9 | 1 | 11% |
| 2. | 30 | 1 | 3% |
| 3. | 5 | 2 | 40% |
| 4. | 18 | 3 | 17% |

TPF-tongue protrusion frequency (protrusions per minute).

Similar results may be obtained when physostigmine, physostigmine sulfite, or physostigmine sulfate is used in place of physostigmine salicylate.

The foregoing specification sets forth preferred embodiments of this invention, however, it will be understood that any other adaptations of this invention are intended to be within the scope of this invention as set forth in the following claims.

What is claimed:

1. A method of treating tardive dyskinesia in a living animal body comprising ingesting into said living animal body in oral dosage form a physostigmine compound selected from the group consisting of physostigmine, physostigmine salicylate, physostigmine sulfite and physostigmine sulfate at intervals of time not less than about four hours apart in an amount effective to relieve the tardive dyskinesia.

2. The method according to claim 1 wherein said oral dosage form is in the form of a tablet.

3. The method according to claim 1 wherein said oral dosage form is in the form of a liquid.

4. The method according to claim 1 wherein said oral dosage form is in the form of a capsule.

5. The method according to claim 1 wherein said oral dosage form is in the form of a powder.

6. The method according to claim 1 wherein said physostigmine compound is in the form of enteric coated particles adapted for timed release.

7. The method according to claim 1 wherein said physostigmine compound is ingested into said living animal body in an amount of 0.000002 to 0.000064 percent by weight of said living animal body.

8. A method of treating tardive dyskinesia in a living animal body comprising ingesting into said living animal body in oral dosage form from about 5.0 to about 20.0 milligrams daily of a physostigmine compound selected from the group consisting of physostigmine, physostigmine salicylate, physostigmine sulfite and physostigmine sulfate at intervals of time not less than about four hours apart in incremental amounts effective to relieve the tardive dyskinesia.

9. A method of treating tardive dyskinesia in a living animal body comprising ingesting into said living animal body on a three times per day time schedule about 15 to 20 milligrams total of physostigmine salicylate in the form of tablets containing about one milligram each of active physostigmine salicylate.

10. A method of treating tardive dyskinesia in a living animal body comprising ingesting into said living animal body at intervals of time not less than about four hours apart an oral dosage containing about 0.5 to about 32.0 milligrams of a physostigmine compound selected from the group consisting of physostigmine, physostigmine salicylate, physostigmine sulfite and physostigmine sulfate.

* * * * *